United States Patent [19]

Veronesi

[11] Patent Number: 4,748,174

[45] Date of Patent: May 31, 1988

[54] WATER SOLUBLE SALTS OF AN NSAID WITH MEGLUMINE/GLUCAMINE

[75] Inventor: Paolo A. Veronesi, Milan, Italy

[73] Assignee: Therapicon s.r.l., Milan, Italy

[21] Appl. No.: 363

[22] Filed: Jan. 5, 1987

[30] Foreign Application Priority Data

Jan. 3, 1986 [IT] Italy .................... 19004 A/86

[51] Int. Cl.$^4$ .............. C07D 279/02; C07D 231/56; C07D 333/22; C07D 207/323; A61K 31/54; A61K 31/44; A61K 31/415; A61K 31/615

[52] U.S. Cl. .......................... 514/226.5; 514/555; 514/352; 514/448; 514/407; 514/411; 514/365; 514/428; 514/427; 260/501.15; 260/501.17; 260/501.16; 546/310; 548/562; 548/565; 548/187; 548/432; 548/372; 548/444; 549/72; 544/49

[58] Field of Search ............... 260/501.15, 501.17, 260/501.16; 514/555, 352, 411, 225, 427; 546/310; 548/562, 187, 372; 549/72; 544/49

[56] References Cited

U.S. PATENT DOCUMENTS 4,602,039  7/1986  Cavazza ............... 260/501.13

Primary Examiner—John M. Ford
Attorney, Agent, or Firm—Burns, Doane, Swecker & Mathis

[57] ABSTRACT

The water soluble acid addition salts of an NSAID, such as acetylsalicylic acid, fenbufen, diflunisal, piroxicam, naproxen, or the like, with either glucamine or meglumine (N-methylglucamine) are useful anti-inflammatory and analgesic drugs, well adopted for parenteral, oral, rectal or topical administration.

34 Claims, No Drawings

WATER SOLUBLE SALTS OF AN NSAID WITH MEGLUMINE/GLUCAMINE

SUMMARY OF THE INVENTION

The present invention relates to novel water soluble acid addition salts of meglumine and glucamine with acetylsalicylic acid, bucloxic acid, flufenamic acid, mefenamic acid, niflumic acid, tiaprofenic acid, tolfenamic acid, bendazac, carprofen, ketoprofen, diclofenac, diflunisal, etodolac, fenbufen, fenoprofen, fentiazac, flurbiprofen, isoxicam, naproxen, pirprofen, piroxicam, sulindac, suprofen, tenoxicam, tolmetin, and zomepirac, and pharmaceutical compositions comprised thereof for parenteral, oral, rectal and topical administration to mammalian organisms in need of such treatment.

Many of the non-steroidal anti-inflammatory and analgesic drugs (NSAIDs) known to this art are either insoluble or only sparingly soluble in water and, consequently, are not suitable for parenteral pharmaceutical preparations.

It has now been determined that the acid addition salts of meglumine and glucamine with the aforesaid NSAIDs are not only admirably water soluble, permitting the parenteral administration thereof, but also permit, by oral administration, a more rapid and complete rate of absorption at the gastrointestinal level, thereby improving indirectly the gastric tolerance of such salts and thus potentiating the anti-inflammatory and analgesic activity without adversely affecting the original pharmacological activity of the NSAID.

The substantial difference between the salts according to the invention (being comprised of both acidic and carbamic functions) and their parent NSAID molecules, is principally physical in nature, namely, marked water solubility, in addition to being structurally quite remote therefrom.

DETAILED DESCRIPTION OF THE PREFERRED EMBODIMENTS OF THE INVENTION

More particularly according to the present invention, the acid addition salts according hereto, prepared by salifying the amino function of meglumine and glucamine with the carboxylic or carbamidic radicals of the noted anti-inflammatory and analgesic drugs, in equimolecular amounts, are characterized by the following general formula (I):

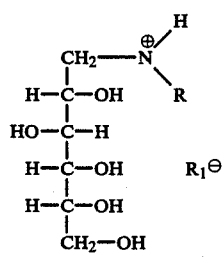

wherein R is —H (glucamine) or —CH$_3$ (meglumine), and R$_1$ is one of the NSAIDs:

ACETYLSALICYLIC ACID: C$_9$H$_8$O$_4$

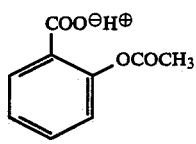
(II)

BUCLOXIC ACID: C$_{16}$H$_{19}$ClO$_3$

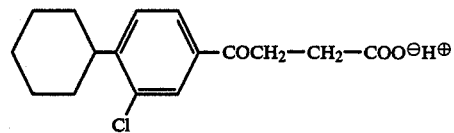
(III)

FLUFENAMIC ACID: C$_{14}$H$_{10}$F$_3$NO$_2$

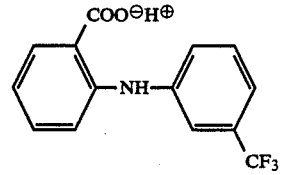
(IV)

MEFENAMIC ACID: C$_{15}$H$_{15}$NO$_2$

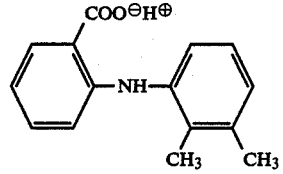
(V)

NIFLUMIC ACID: C$_{13}$H$_9$F$_3$N$_2$O$_2$

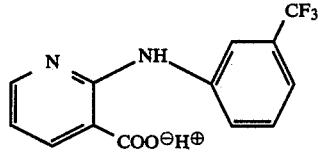
(VI)

TIAPROFENIC ACID: C$_{14}$H$_{12}$O$_3$S

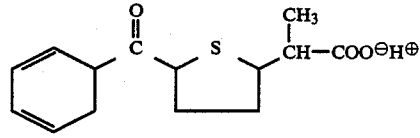
(VII)

TOLFENAMIC ACID: C$_{14}$H$_{12}$ClNO$_2$

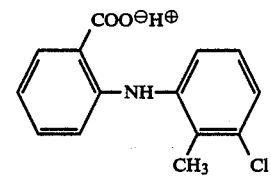
(VIII)

BENDAZAC: C$_{16}$H$_{14}$N$_2$O$_3$

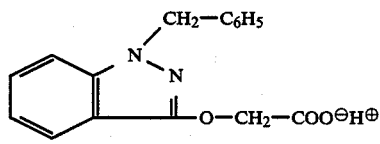
(IX)

CARPROFEN: C$_{15}$H$_{12}$ClNO$_2$

-continued
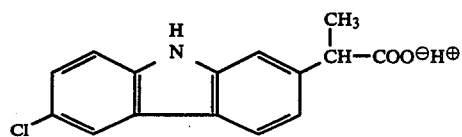
KETOPROFEN: $C_{16}H_{14}O_3$
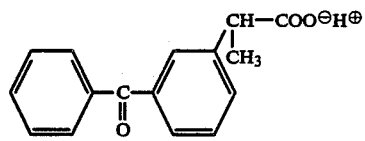
DICLOFENAC: $C_{14}H_{11}Cl_2NO_2$
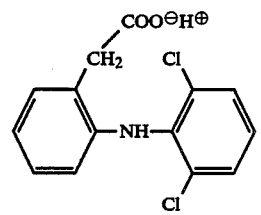
DIFLUNISAL: $C_{13}H_8F_2O_3$
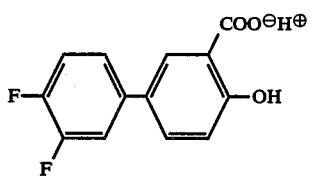
ETODOLAC: $C_{18}H_{22}NO_3$
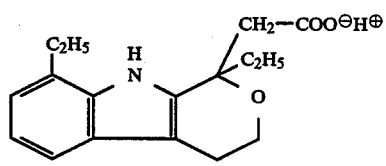
FENBUFEN: $C_{16}H_{14}O_3$
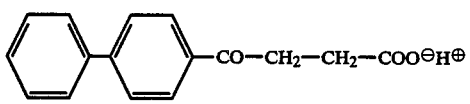
FENOPROFEN: $C_{15}H_{14}O_3$
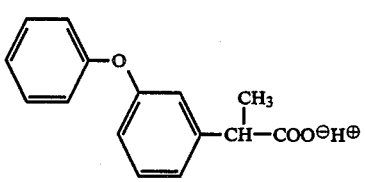
FENTIAZAC: $C_{17}H_{12}ClNO_2S$
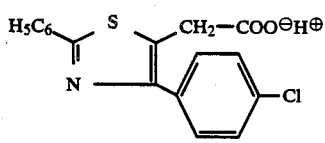
FLURBIPROFEN: $C_{15}H_{13}FO_2$
-continued
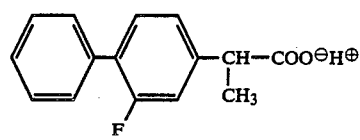
ISOXICAM: $C_{14}H_{13}N_3O_5S$
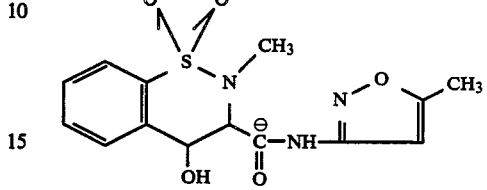
NAPROXEN: $C_{14}H_{14}O_3$
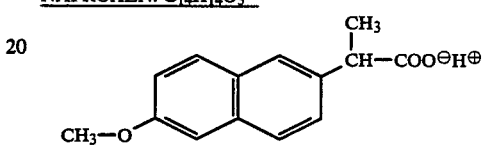
PIRPROFEN: $C_{13}H_{14}ClNO_2$
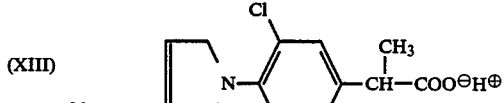
PIROXICAM: $C_{15}H_{13}N_3O_4S$
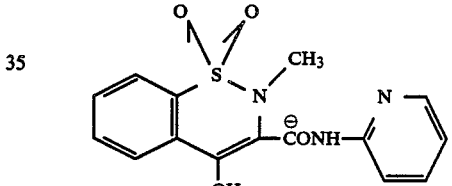
SULINDAC: $C_{20}H_{17}FO_3S$
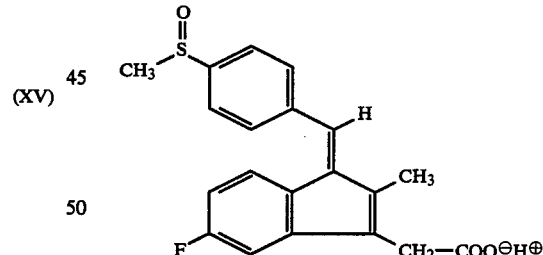
SUPROFEN: $C_{14}H_{12}O_3S$
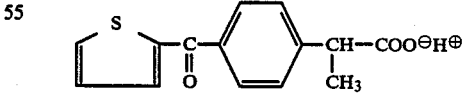
TENOXICAM: $C_{13}H_{11}N_3O_4S_2$
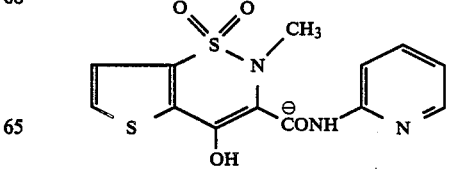
TOLMETIN: $C_{15}H_{15}NO_3$

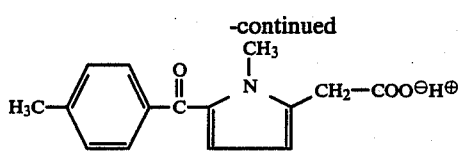

(XXVI)

ZOMEPIRAC: C$_{15}$H$_{14}$ClNO$_3$

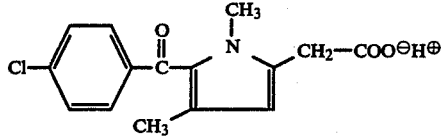

(XXVII)

The water soluble salts according to the invention are prepared by direct reaction between meglumine or glucamine with the NSAIDs R$_1$ in equimolecular amounts.

For example, an aqueous solution of meglumine or glucamine is slowly added to equimolecular amounts of R$_1$, previously prepared as a solution in an organic solvent (being sparingly or almost insoluble in water) or as a finely ground powder. In the event R$_1$ is unstable in aqueous solutions, it is alternatively possible to use ethanol or another organic solvent as the reaction medium. The final products obtained in solution may be separated from the solution by well known techniques, such as pecipitation or crystallization, using other suitable solvents, or by lyophilization.

The precipitation may also be carried out using an excess of organic solvent, such as, for example, benzene, toluene, acetone, methylene chloride or like materials, while altering the temperature, and therefore the salts of general formula (I) are separated from the reaction mixture by filtration, washed and optionally dried in a fluid bed dessicator under nitrogen flow.

The salts according to the invention may be administered as such or in the form of suitable pharmaceutical compositions adopted for parenteral, oral, rectal and topical routes, either alone or associated with other active ingredients. The pharmaceutical compositions containing the salts of the invention may be prepared as tablets, powders, granules, hard or soft gelatine capsules, suspensions, syrups, suppositories, ointments or essentially solutions or injectable powders, to be reconstituted as ready-to-use solutions.

The oral pharmaceutical forms may be prepared using standard methods for the formulation of pharmaceutical compositions adopted for this route. They contain, in addition to one or more active ingredients (I), one or more excipients or organic or inorganic carriers, which should be pharmaceutically acceptable and chemically compatible with the other components thereof. Other materials commonly used for sweetening, flavoring, or preserving the formulations may also be included. For example, tablets may be prepared using inert carriers such as calcium carbonate, sodium carbonate, lactose, talc, granulating or disintegrating agents, i.e., alginic acid, agglutinating agents, e.g., starch, gelatin and gum arabic, lubricating agents, e.g., stearic acid and magnesium stearate. Such tablets may either be coated or uncoated.

The capsules may contain the active ingredient alone, or mixed with solid or liquid carriers such as calcium carbonate, calcium phosphate or kaolin. the powders are prepared by thoroughly mixing the active ingredient with known excipients. Furthermore, the powders may be packaged in packets, boxes or individual sachets, each containing a unit dosage amount of the particular derivative (I).

The granules for the reconstitution of oral liquid compositions are prepared by using diluent carriers soluble in water. The active ingredient (I) is mixed with water soluble carriers such as sucrose, glucose or the like, and with an agglutinating agent, such as mucillage or gum arabic, and added to a solution of gelatin or methylcellulose. The mixture is then passed through a sieve to provide granules, which are thereafter dried. Gum tragacanth is included in the composition when required.

Similarly, the solutions, suspensions, syrups and elixirs may contain one or more active ingredients (I), mixed with any other conventional excipient or carrier used for the preparation of such formulations, such as, for example, suspending agents such as methylcellulose, gum tragacanth and sodium alginate, wetting agents such as lecithin or polyoxyethylenesorbitol, or preservatives such as ethyl or propyl p-hydroxybenzoate.

The liquid preparations may be administered in individual does, such as, for example, one teaspoonful of the preparation, corresponding to 5 ml, which shall contain appropriate predetermined amount of the active substance (I).

The liquid preparations may also be administered in dosage units, such as, for example, an aqueous solution obtained by dissolving a determined quantity of the preparation in water, the same containing a precise amount of active agent. The compositions may also contain one or more coadjuvant materials, such as, for example, sweetening, flavoring, or coloring agents in order to provide acceptable preparations either for testing or visual purposes.

For parenteral administration, pharmaceutical dosage forms may be formulated comprising individual unit doses of each compound as required to elicit the desired therapeutic effect.

For the preparation of such compositions, the general procedures well known to this art are followed. According to such procedures, to obtain parenteral pharmaceutical forms, suitable vials are filled with a predetermined amount of active ingredient in a sterile room, whether lyophilized or as a sterilized powder, and sealed hermetically. The vial may be accompanied by another ampoule containing twice distilled sterile water pro-injection, which will be used as a solvent for the ready-to-use preparation.

Furthermore, the sterile water may also contain an anesthetic and a buffer. Moreover, the injectable preparations, containing the salts of this invention, may also be prepared in single or multiple dose vials.

The appropriate amount of active agent (I) to be used as the analgesic or anti-inflammatory drug will depend upon each particular compound and on the effect desired. Also, the individual doses and the administration intervals likewise depend on the particular active agent and cumulative dose required daily.

In order to further illustrate the present invention and the advantages thereof, the following specific examples are given, it being understood that same are intended only as illustrative and in nowise limitative.

EXAMPLE 1

Preparation of meglumine acetylsalicylate

Acetylsalicylic acid (45 g) was dissolved in 800 ml of ethanol and meglumine (49 g) was slowly added thereto, while maintaining the mixture at room temperature (25°-30° C.) under constant, mild stirring.

The reaction mixture was stirred for 6 hours and evaporated to 100 ml in vacuo and then cooled at 5° C. for one hour. The resulting white microcrystalline precipitate was filtered off. The material removed was dried under nitrogen laminar flow and 89 g of final product were obtained. The compound was identified as meglumine acetylsalicylate.

Molecular weight (M.W.)=375.36

| Analysis: $C_{16}H_{25}NO_9$ | C % | H % | N % |
| --- | --- | --- | --- |
| Calculated: | 51.19 | 6.71 | 3.73 |
| Found: | 51.15 | 6.65 | 3.73 |

Using like procedures, adapting the solvents and the reaction conditions to the different $R_1$ radicals, the other water soluble salts of the invention comprised of the NSAIDs (II) to (XXVII) may be obtained.

EXAMPLE 2

Preparation of fenbufen glucamine 60 g glucamine, dissolved in 180 ml demineralized water, were slowly added to finely ground fenbufen (85 g) by slowly stirring the reaction mixture without exceeding 50° C.

The reaction mixture was stirred for 4 hours, filtered and evaporated to 50 ml in vacuo. The resulting precipitate was separated by filtration and collected. By adding acetone (40 ml), further material was precipitated from the residual solution, filtered, collected and added to the first precipitate. The material obtained was dried under nitrogen laminar flow without exceeding 40° C.; 139 g of final product, identified as fenbufen glucamine, were obtained.

Molecular weight (M.W.)=435.48

| Analysis: $C_{22}H_{29}NO_8$ | C % | H % | N % |
| --- | --- | --- | --- |
| Calculated: | 60.67 | 6.71 | 3.21 |
| Found: | 60.51 | 6.73 | 3.20 |

Similarly, other derivatives of the invention may also be obtained by reacting meglumine and glucamine with the compounds (II) to (XXVII).

EXAMPLE 3

Preparation of diflunisal meglumine 83 grams of diflunisal, dissolved in 500 ml ethanol, were added to an aqueous solution of 65 g meglumine, by stirring slowly and at room temperature (20° C.), and the reaction mixture was maintained under stirring for 4 hours until the reaction was complete. After cooling at 7° C., the resulting white precipitate was filtered and washed with small quantities of ethanol. After drying, 139 g of diflunisal meglumine were obtained as a white microcrystalline powder.

| Molecular weight: $C_{20}H_{25}F_2NO_8$ | C % | H % | F % | N % |
| --- | --- | --- | --- | --- |
| Calculated: | 59.93 | 5.65 | 8.53 | 3.14 |
| Found: | 59.89 | 5.61 | 8.49 | 3.15 |

Using like procedures, the other salts of the invention may also be obtained by reacting meglumine and glucamine with the other compounds (II) to (XXVII).

EXAMPLE 4

Preparation of parenteral compositions of piroxicam meglumine (A) Ampoules

| | |
| --- | --- |
| (i) piroxicam meglumine (active ingredient) | 15.90 mg |
| (ii) polyethylene glycol 200 | 300.00 mg |
| (iii) sodium metabisulfite | 1.00 mg |
| (iv) sodium ethylenediamine tetraacetate | 0.05 mg |
| (v) distilled water pro-injection | q.s. to 1.00 ml |

Similarly, parenteral preparations may be obtained by using the other compounds of general formula (I) in the appropriate therapeutic amounts.

(B) Vials

The vials may be obtained by filling, with the same amounts of piroxicam meglumine (as lyophilized powder), suitable vials and sealing them in a sterile room using special rubber plugs. By using distilled water introduced with a syringe through the rubber plug, it is possible to obtain a ready-to-use solution.

EXAMPLE 5

Preparation of tablets containing diflunisal meglumine

| | |
| --- | --- |
| (i) Diflunisal meglumine (active ingredient) | 890.8 g |
| (ii) lactose | 250.0 g |
| (iii) maize starch | 50.0 g |
| (iv) colloidal silica | 20.0 g |
| (v) soluble starch | 30.0 g |
| (vi) magnesium stearate | 5.0 g |

The active ingredient was thoroughly mixed with a portion of the excipients and granulated with an aqueous solution of soluble starch. The dried granulate was added to the remaining excipients and the entire mass was converted into tablets. 1000 tablets of diflunisal meglumine (average weight 1.25 g) each containing 890 mg of active ingredient or 200 tablets (average weight 0.637 g), each containing 445 mg of diflunisal meglumine, were produced.

In similar fashion may be prepared corresponding tablets containing appropriate dosages of the other derivatives of general formula (I).

EXAMPLE 6

Preparation of granules of naproxen meglumine

The addition salts of the invention may also be prepared as granules for the reconstitution of a liquid preparation used in individual dosages.

| | |
| --- | --- |
| (i) Naproxen meglumine (active ingredient) | 925.0 mg |
| (ii) sucrose | 5200.0 mg |
| (iii) citric acid | 10.0 mg |
| (iv) trisodium citrate | 90.0 mg |
| (v) sodium p-hydroxybenzoate | 25.0 mg |
| (vi) sweetening and flavoring agents | q.s. |

Sorbitol may be used instead of sucrose to permit administration of the granules to diabetic patients.

The granules, prepared using techniques well known to this art, are packed in sachets, each containing 925 mg of naproxen meglumine. The content of each sachet, dissolved in water, is equivalent to the individual unitary dose of the active ingredient considered above.

Using like procedures, sachets containing the other derivatives of general formula (I) may be produced.

While the invention has been described in terms of various preferred embodiments, the skilled artisan will appreciate that various modifications, substitutions, omissions, and changes may be made without departing from the spirit thereof. Accordingly, it is intended that the scope of the present invention be limitedly solely by the scope of the following claims, including equivalents thereof.

What is claimed is:

1. A water soluble acid addition salt of meglumine or glucamine and one of the NSAIDs, acetylsalicylic acid, bucloxic acid, flufenamic acid, mefanamic acid, niflumic acid, tiaprofenic acid, tolfenamic acid, bendazac, carprofen, ketoprofen, diclofenac, diflunisal, etodolac, fenbufen, fenoprofen, fentiazac, flurbiprofen, isoxicam, naproxen, pirfrofen, piroxicam, sulindac, suprofen, tenoxicam, tolmetin, or zomepirac.

2. The acid addition salt as defined by claim 1, the NSAID being acetylsalicylic acid.

3. The acid addition salt as defined by claim 1, the NSAID being bucloxic acid.

4. The acid addition salt as defined by claim 1, the NSAID being flufenamic acid.

5. The acid addition salt as defined by claim 1, the NSAID being mefenamic acid.

6. The acid addition salt as defined by claim 1, the NSAID being niflumic acid.

7. The acid addition salt as defined by claim 1, the NSAID being tiaprofenic acid.

8. The acid addition salt as defined by claim 1, the NSAID being tolfenamic acid.

9. The acid addition salt as defined by claim 1, the NSAID being bendazac.

10. The acid addition salt as defined by claim 1, the NSAID being carprofen.

11. The acid addition salt as defined by claim 1, the NSAID being ketoprofen.

12. The acid addition salt as defined by claim 1, the NSAID being diclofenac.

13. The acid addition salt as defined by claim 1, the NSAID being diflunisal.

14. The acid addition salt as defined by claim 1, the NSAID being etodolac.

15. The acid addition salt as defined by claim 1, the NSAID being fenbufen.

16. The acid addition salt as defined by claim 1, the NSAID being fenoprofen.

17. The acid addition salt as defined by claim 1, the NSAID being fentiazac.

18. The acid addition salt as defined by claim 1, the NSAID being flurbiprofen.

19. The acid addition salt as defined by claim 1, the NSAID being isoxicam.

20. The acid addition salt as defined by claim 1, the NSAID being naproxen.

21. The acid addition salt as defined by claim 1, the NSAID being pirfrofen.

22. The acid addition salt as defined by claim 1, the NSAID being piroxicam.

23. The acid addition salt as defined by claim 1, the NSAID being sulindac.

24. The acid addition salt as defined by claim 1, the NSAID being suprofen.

25. The acid addition salt as defined by claim 1, the NSAID being tenoxicam.

26. The acid addition salt as defined by claim 1, the NSAID being tolmetin.

27. The acid addition salt as defined by claim 1, the NSAID being zomepirac.

28. A pharmaceutical composition of matter comprising the acid addition salt as defined by claim 1, and a pharmaceutically acceptable carrier therefor.

29. The composition of matter as defined by claim 28, adopted for parenteral administration.

30. The composition of matter as defined by claim 28, adopted for oral administration.

31. The composition of matter as defined by claim 28, adopted for rectal administration.

32. The composition of matter as defined by claim 28, adopted for topical administration.

33. A method for eliciting an anti-inflammatory or analgesic response in a mammalian organism in need of such treatment, comprising administering to such organism an anti-inflammatory or analgesically effective amount of the acid addition salt as defined by claim 1.

34. A method for eliciting an anti-inflammatory or analgesic response in a mammalian organism in need of such treatment, comprising administering to such organism an anti-inflammatory or analgesically effective amount of the composition of matter as defined by claim 28.

* * * * *